(12) United States Patent
Smith (10) Patent No.: US 6,426,041 B1
(45) Date of Patent: Jul. 30, 2002

(54) MULTIPURPOSE SURGICAL INSTRUMENT TRAY

(76) Inventor: Sharon G. Smith, 7 Cross St., South Easton, MA (US) 02357

(*) Notice: Subject to any disclaimer, the term of this patent is extended or adjusted under 35 U.S.C. 154(b) by 0 days.

(21) Appl. No.: 09/721,312

(22) Filed: Nov. 22, 2000

Related U.S. Application Data
(60) Provisional application No. 60/166,962, filed on Nov. 23, 1999.

(51) Int. Cl.$^7$ .................................................. A61L 2/06
(52) U.S. Cl. .......................... 422/28; 422/297; 422/300; 206/223; 206/363; 206/369; 206/438; 206/565
(58) Field of Search ................................. 422/297, 300, 422/28, 310; 206/370, 363, 364, 369, 438, 565

(56) References Cited

U.S. PATENT DOCUMENTS

| | | | |
|---|---|---|---|
| D218,077 S | * | 7/1970 | Gabriel .......................... D83/1 |
| 3,802,555 A | * | 4/1974 | Gratsy et al. ................ 206/223 |
| 3,868,016 A | | 2/1975 | Szpur |
| 3,925,014 A | | 12/1975 | Langdon |
| 4,046,254 A | | 9/1977 | Kramer |
| D248,871 S | | 8/1978 | Forsmann |
| 4,229,420 A | | 10/1980 | Smith |
| 4,266,669 A | | 5/1981 | Watson |
| 4,342,391 A | | 8/1982 | Schainholz |
| 4,541,992 A | | 9/1985 | Jerge |
| 4,577,755 A | | 3/1986 | Ramsay |
| 5,005,590 A | | 4/1991 | Floridge, Jr. |
| 5,031,768 A | | 7/1991 | Fischer |
| 5,170,804 A | | 12/1992 | Glassman |
| 5,195,538 A | | 3/1993 | Floridge, Jr. |
| 5,284,632 A | * | 2/1994 | Kudla et al. ................. 422/297 |
| 5,294,413 A | | 3/1994 | Riihimaki |
| 5,322,072 A | | 6/1994 | Harrison |
| 5,339,955 A | | 8/1994 | Hogran |
| 5,384,103 A | | 1/1995 | Miller |
| D360,697 S | | 7/1995 | Riihimaki |
| 5,433,929 A | | 7/1995 | Riihimaki |
| 5,451,380 A | | 9/1995 | Zinnanti |
| D376,652 S | | 12/1996 | Hunt |

* cited by examiner

Primary Examiner—Robert J. Warden, Sr.
Assistant Examiner—Sean E. Conley
(74) Attorney, Agent, or Firm—Lambert & Associates; Gary E. Lambert; Edward Timmer

(57) ABSTRACT

A sterilizable, surgical instrument tray that can deliver, in an instant nearly, 100 ringed surgical instruments held and displayed in a perpendicular fashion in a space and manner similar to that used by surgical scrub nurses on their operating room back tables, as well as hold and display with easy access, a number of forceps, knife handles and retractors. A surgical instrument tray, capable of retaining all the general/major/trauma instruments and arranging these instruments in such a way that said tray may be placed in the operating room in sterile manner, being ready for operational usage. Due to the design and construction of the tray, with recessed sections of applicable shape and size to accommodate certain instruments, upon extraction of the instruments from the tray, the instruments are in ready position to be relayed to the person performing the operation, with no further manipulation of the instruments. Thus, the device is delivered in the above-described state, available for use upon delivery into an operating room setting with no additional setup time and personnel are required. The tray can be employed in one and two tier embodiments.

19 Claims, 9 Drawing Sheets

MULTIPURPOSE SURGICAL INSTRUMENT TRAY

CROSS REFERENCE TO RELATED APLICATIONS

This invention relates to Provisional Patent No.: 60/166962, filed Nov. 23, 1999.

FIELD OF THE INVENTION

This invention relates generally to the field of surgical instruments and specifically to trays for transporting sterile, surgical instruments to an operating room and storing these sterile instruments for ready use during surgical procedures.

BACKGROUND OF THE INVENTION

Storage and sterilization systems for dental, medical and orthopedic instruments are well known in the art. Many apparatuses employing manners of stacking and spacing surgical instruments have been devised. In the realm of medical surgical instruments, storage trays for sterilization and storage of instruments employed in individualized procedures have been devised and utilized. These systems can be limited in that the systems are not designed to accommodate certain procedures. The need for these procedures often arises due to complications from the initial operation room procedure. The General Instrument Kit utilized in many of the operating room procedures performed today does not possess the versatility to handle these changes in the operating room procedures.

The term General Instrument Kit includes any instrument kit that contains ringed instruments such as snaps, Kellys, Ailises, Babcocks, Kochers, needle holders, sponge sticks, scissors etc. General Instrument Kit shall include Gyn, Thoracic, Trauma, Vascular but not exclude others not mentioned. The current way of setting up general/major/trauma instruments for a surgical case is time consuming. Basically what happens is, instruments are packaged and sterilized by Central Supply Department personnel. These packages of instruments are sent to the Operating Room in preparation for a surgical procedure. In the operating room a back table is lined with sterile drapes much like a table cloth. On top of this sterile drape many sterile supplies are opened and placed on this back table. One surgical nurse does a surgical scrub, puts on a sterile gown and gloves and begins to rearrange the multiple sterile supplies needed for the case. First the back table is lined with towels and one or two towels are made into tight rolls on which will rest the 50 to 100 ringed instruments in a perpendicular manner.

If this roll is not made tight enough or too large, the instruments frequently fall into each other or off the roll and are difficult to manage especially if the case is an emergency. The ringed instruments are removed from the sterile buckets from Central Supply, unstrung from the two long armed "stringers" by laying them along the rolled towels in a perpendicular fashion. These stringers have rotating clamps on either end to stop instruments from failing off. Frequently, especially if rushed, instruments get caught on these clamps. Instruments that are not strung or are loose in the bottom of the buckets, such as forceps, knife handles, retractors or scissors, need to be gathered up, arranged and organized on the back table. All this needs to take place before a complete count of all instruments and sponges can be done. This whole process is not only time consuming but can also be stressful, especially in an emergency.

Many Scrub Nurses will also set up the instruments in their own personal styles which can become awkward if another scrub nurse relieves and a specific instrument cannot be located during the case or for the closing count, when all instruments have to be accounted for. With many cases being done by Laparoscopic methods, it is necessary to either have a Major Instrument Kit set up in case it is needed and the procedure becomes an Open case or take the time while the procedure is under way to set up and count these instruments. Both of these processes can take approximately ten minutes or longer. Almost 99.5% of the time a Laparoscopic case does not turn into an open case and these Major Instruments are gathered up at the end of the case, mostly unused, and are sent back down to Central Supply to be reprocessed, thus making unnecessary work for both departments.

Although there are many apparatuses for retaining surgical instruments, commonly known as instrument trays on the market, most of these are made for specific, specialty instruments such as Orthopedics or very fine Plastic or Vascular instruments and Laparoscopic instruments. The trays for very fine or delicate instruments tend to have the instruments stacked one on top of the next or simply placed on a rubber mat. The Orthopedic instruments are held in craters that are molded specifically for their individual shapes. Those that are held in a perpendicular manner are held with forged metal or rubber type cleats. If these methods were used to hold a General Instrument Kit, the amount of cleats needed to hold the 50–100 ringed instruments found in the kits to which I am referring would be prohibitive in size. This many cleats would also be very costly to manufacture.

What is needed is a surgical instrument tray, capable of retaining all the general/major/trauma instruments and arranging theses instruments in such a way that said tray may be placed in the operating room in sterile manner, being ready for operational usage.

SUMMARY OF THE INVENTION

The instant invention comprises a sturdy plastic or rubberized mat or tray that holds and displays in an instant, substantially all the instruments generally found in a General Instrument Kit. The advantages of this invention are that the ringed instruments found in a General Instrument Kit are held and displayed with handles disposed in a perpendicular manner, similar to that used by scrub nurses on their back tables. Due to the design of the tray, upon extraction of the non ringed instruments from the tray, the instruments are in ready position to be relayed to the person performing the operation, with no further manipulation of the instruments. The device is delivered in the above described state and is thus available for use upon delivery into an operating room setting. No additional setup time and personnel are required.

The tray may be configured in multiple embodiments, two of which are the single tiered and the double tiered arrangement. In the singled tiered preferred embodiment, the long horizontal rectangular channel 2, FIG. 1 at the front of my instrument tray allows for easy loading and counting of ringed instruments. The section dividers 1 allow for support to hold the ringed instruments in a perpendicular position. A recessed section 3 parallel to the horizontal channel 2 allows for easy removal of the ringed instruments and allows for positioning of the instruments for proper operating room instrument handling procedures. This instrument tray also holds and displays, for easy access, multiple forceps, knife handles and retractors, all of this with taking up minimal space on an operating room back table.

In the double or two tiered embodiment, the same ability to retain multiple instruments in proper operating room ready state is found, however the double tiered embodiment may be configured to provide even more area for storage of instruments.

DETAILED DESCRIPTION OF THE PREFFERED EMBODIMENT

Many prior art instrument trays contain grooves or recesses, designed for individual instruments. Many of these trays include mechanisms designed to hold individual instruments and although these trays are adequate for storage of surgical instruments, their capacity to hold a large quantity of varying instruments in operation ready position is severely limited. The instant invention encompasses upwardly concave grooves, capable of retaining multiple tools, disposed in the position they would normally need to be placed into for operational use. This instant invention also contains movable or fixed section dividers which allow the instruments to remain in a ready state no matter how many instruments have been removed from tray. This not only saves space, it saves precious operating room set up time, since the instruments are readily available and sterile upon removal of the protective covering. No where does the importance of this feature shine more than when a Laparoscopic case turns into an open case. No searching through the General kit is needed, since the instruments are already in place.

The instrument tray can be made of rubberized, plastic or metal material that is capable of normal sterilization techniques. It may either be reusable or disposable. In one preferred embodiment, the instrument tray may be approximately 54 cm long×42 cm wide and approximately 5 cm deep. It may be made in different sizes to accommodate larger or smaller sized instrument kits. In all configurations, the instrument tray is disposed with holes to for flow during the sterilization process.

The instrument tray comprises multiple configurations. In one preferred embodiment, the instrument tray may be a single tiered entity, as illustrated in FIG. 1–4. The single tiered tray comprises two opposed, longitudinally oriented sides 8 and two opposed widthwise oriented sides 9, the longitudinally oriented sides 9 being substantially longer than the widthwise oriented sides 8. The following description comprises the components of a single tiered tray.

The single tiered instrument tray comprises one longitudinally oriented, mortised rectangular channel 2, aligned substantially parallel and at a close distance to one of said longitudinally oriented sides of said tray. The channel may extend approximately 3 cm, deep and has four sides. The channel substantially encompasses the length of said longitudinal wall with the exception of comprising two end members, disposed perpendicularly to the longitudinal direction of the channel 2. The channel 2 is designed such that an individual ring handled instrument or a plurality of ring handled instruments may fit into said channel 2. The instruments are thus retained snugly by the handle in the proper position for operating room procedures.

Figure 4:
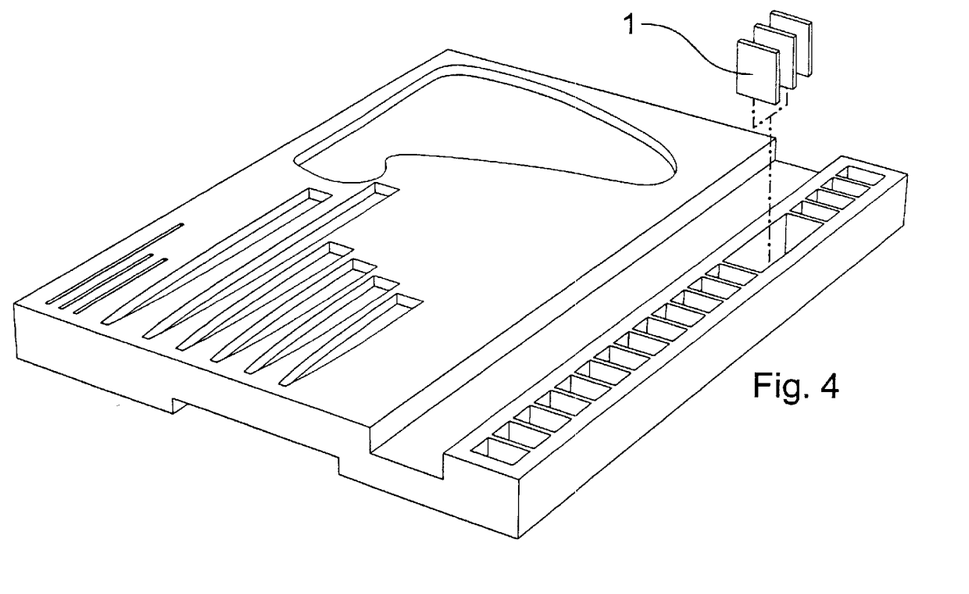
FIG. 4 is a perspective view of the single tiered proffered embodiment of the apparatus showing some of the section dividers removed.

A plurality of section dividers 1 as illustrated in FIG. 4, which may be fixed or removably attached and disposed in a manner perpendicular to the length of the first channel 2 and align parallel to said end members within said rectangular channel 2. These section dividers 1 may be set apart at intervals of approximately 2 cm, or longer depending on the number of instruments to be held in place, wherein said section dividers are adapted to releasably and securely retain at least two or more ring handled instrument in a space defined by consecutively placed dividers. The sections dividers 1 may also constitute a fixed member of the tray.

A second rectangular channel 3, which runs the entire longitudinal distance of the tray, is positioned a distance from said first rectangular channel 2 and a further distance from said longitudinally oriented side. This second channel 3 is designed to allow the operating room assistant the ability to get a proper grip on the ring handled instruments in order to relay the instruments to the person performing the operation in accordance with proper operating room procedures.

On the bottom of the tray, located about the central axis in the longitudinal direction, is a groove section cutout 4. This cutout 4 is there to assist in handling and set up for sterilization of the instruments contained in the tray.

Figure 1:
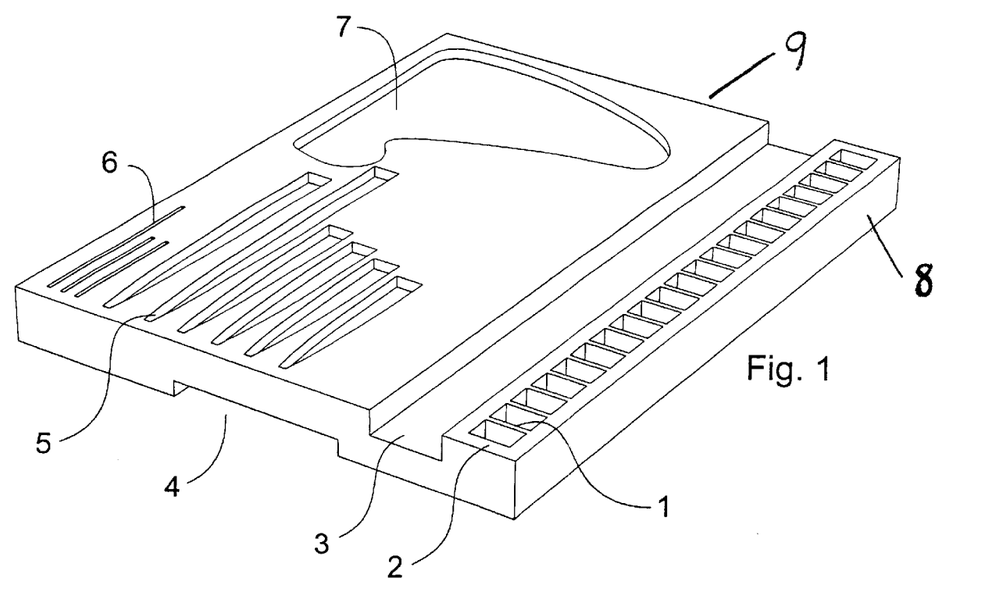
FIG. 1 is a perspective view of the single tiered proffered embodiment of the apparatus, with no instruments positioned in the apparatus.

The remaining top surface of the tray has numerous cutouts designed to retain other types of operating room instruments. In FIG. 1, a preferred embodiment illustrates a large mortised triangular groove including arcuate edges 7, disposed at a distance from said second rectangular channel 3 and on the opposing side from said first rectangular channel 2. Said triangular groove may be utilized to releasably retain instruments that comprise a straight handle and an arcuate operational surface. In one preferred embodiment, the instruments contained in said triangular groove 7 may be retractors. Up to and including eight retractors may be contained in any one triangular groove.

Aligned parallel to said second rectangular groove 3 are a series of smaller, mortised trapezoidal grooves 5, designed to releasably retain cylindrically shaped or flat, dual handled instruments. As seen in FIG. 4, the length of these grooves is regulated by the size and positioning of said triangular groove 7, as these trapezoidal grooves 5 span in a direction perpendicular to said triangular groove 7. The trapezoidal shape of these slots acts as a bevel to allow a user to easily remove an instrument from the groove. In one preferred embodiment, these grooves may be adapted to contain forceps or other such instruments. Up to six of these slots may be disposed, these slots varying in size to accommodate different sizes of instruments.

Figure 2:
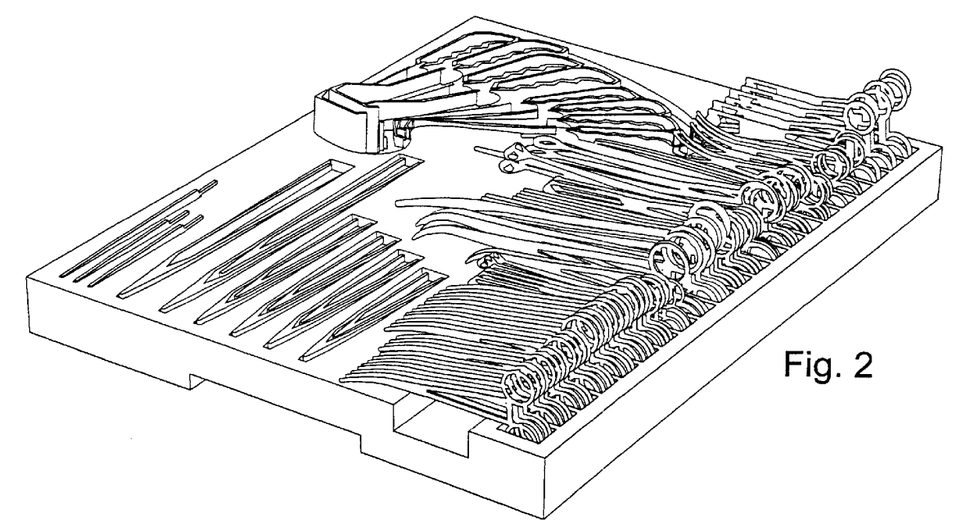
FIG. 2 is a perspective view of the single tiered proffered embodiment of the apparatus, with the instruments from a General Major Kit.
Figure 3:
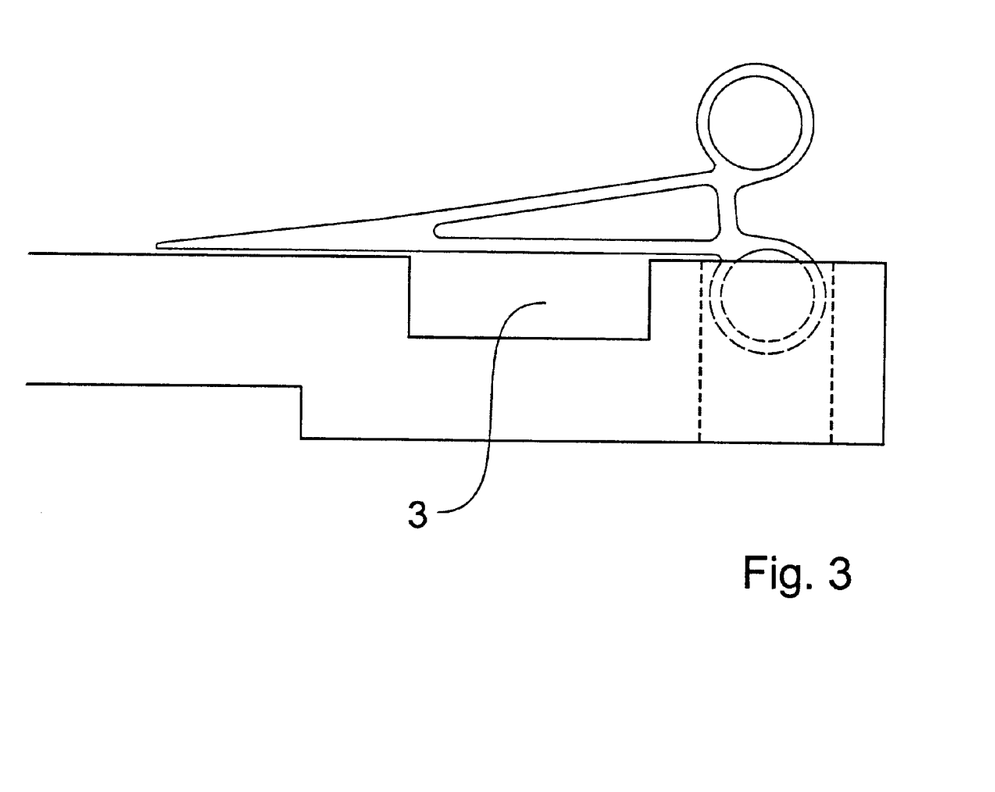
FIG. 3 is a left side elevation view of the single tiered proffered embodiment of the apparatus, showing the recessed section 3 that allows for easy removal of the ringed instruments and how the ringed instruments nest in the horizontal rectangular channel.

Finally, the single tiered embodiment may comprise a series of rectangular slots 6, smaller in length and width than said trapezoidal slots 5. These slots may be utilized to contain such instruments as knife handles. FIG. 2 illustrates the single tiered embodiment fully loaded with proper instruments disposed in full operation room configuration.

Figure 5:
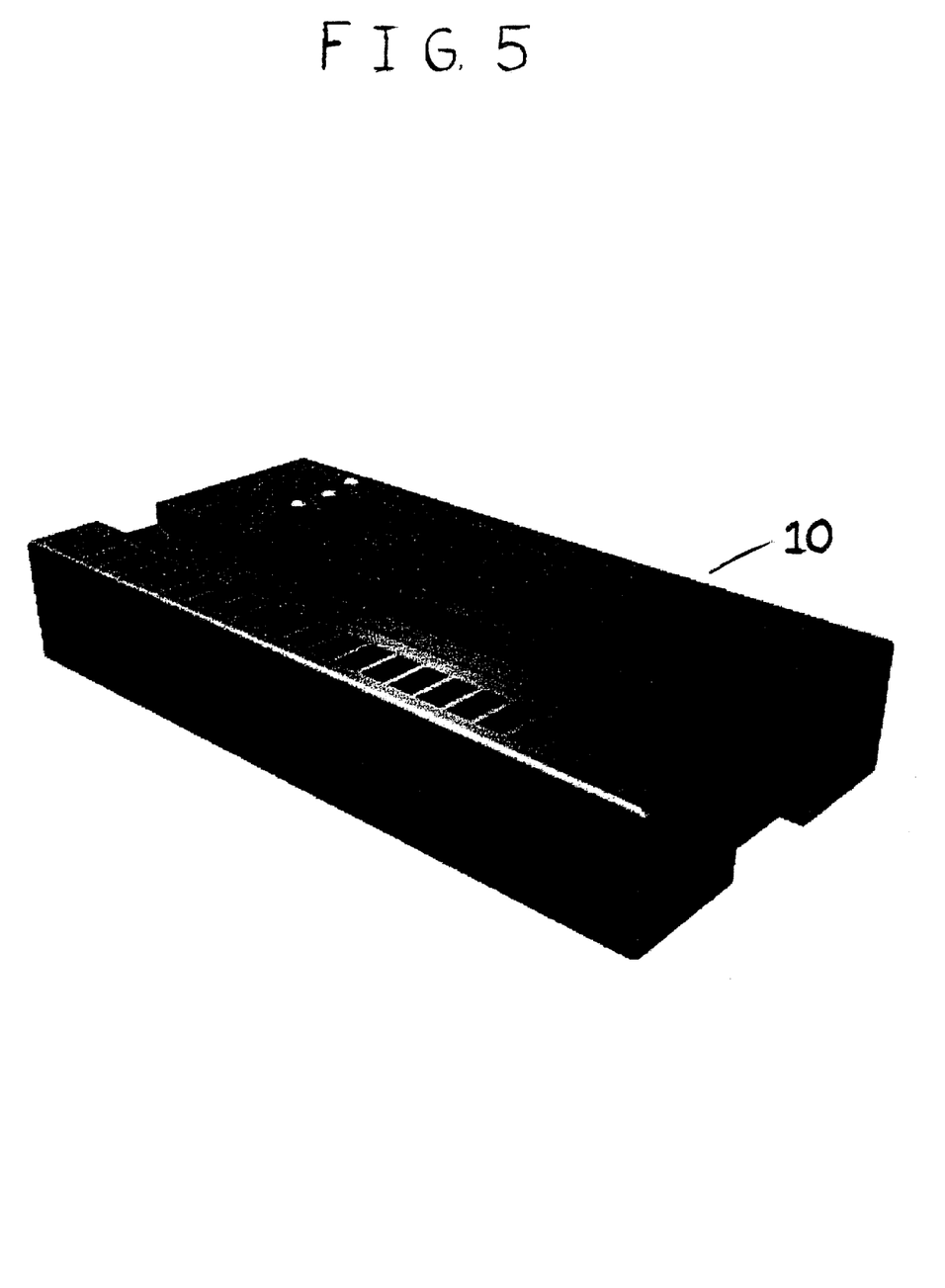
FIG. 5 is a perspective view of the double tiered proffered embodiment of the apparatus, with both tiers shown stacked and no instruments positioned in the apparatus.
Figure 6:
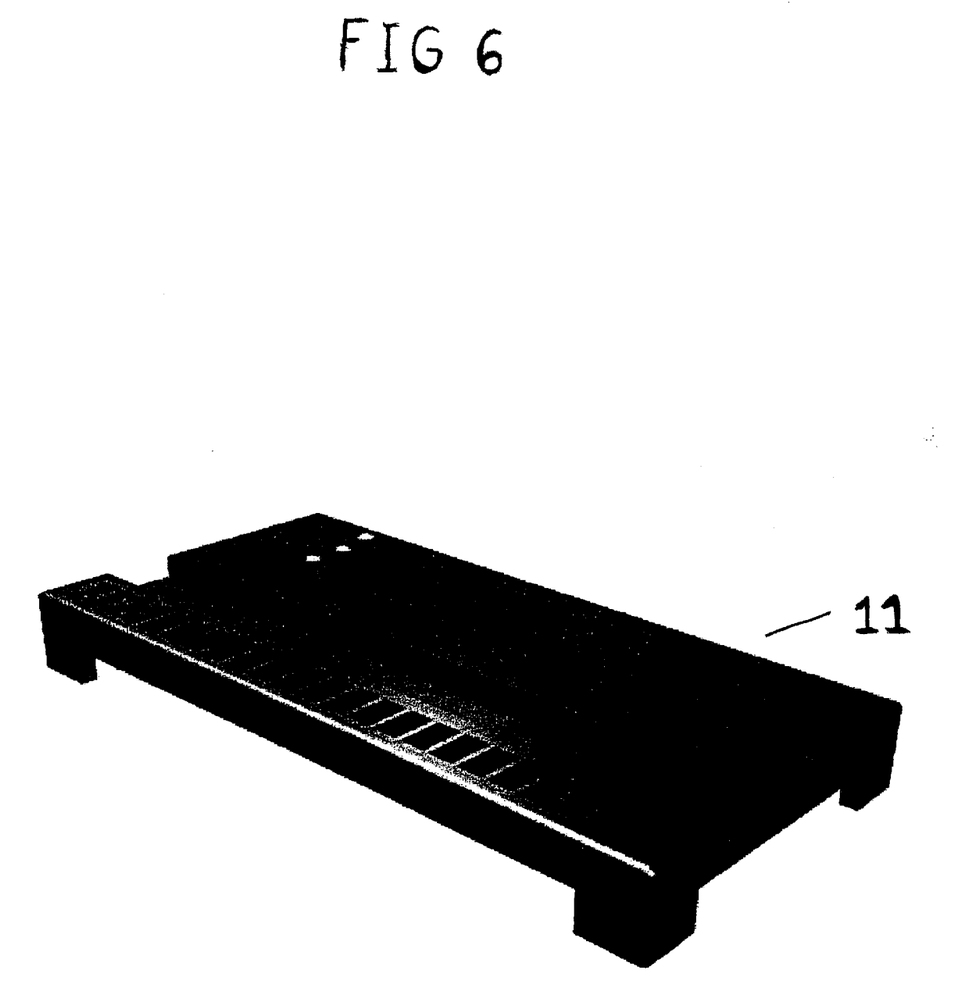
FIG. 6 is a perspective view of the top tier of the double tiered proffered embodiment of the apparatus, with no instruments positioned in the apparatus.
Figure 7:
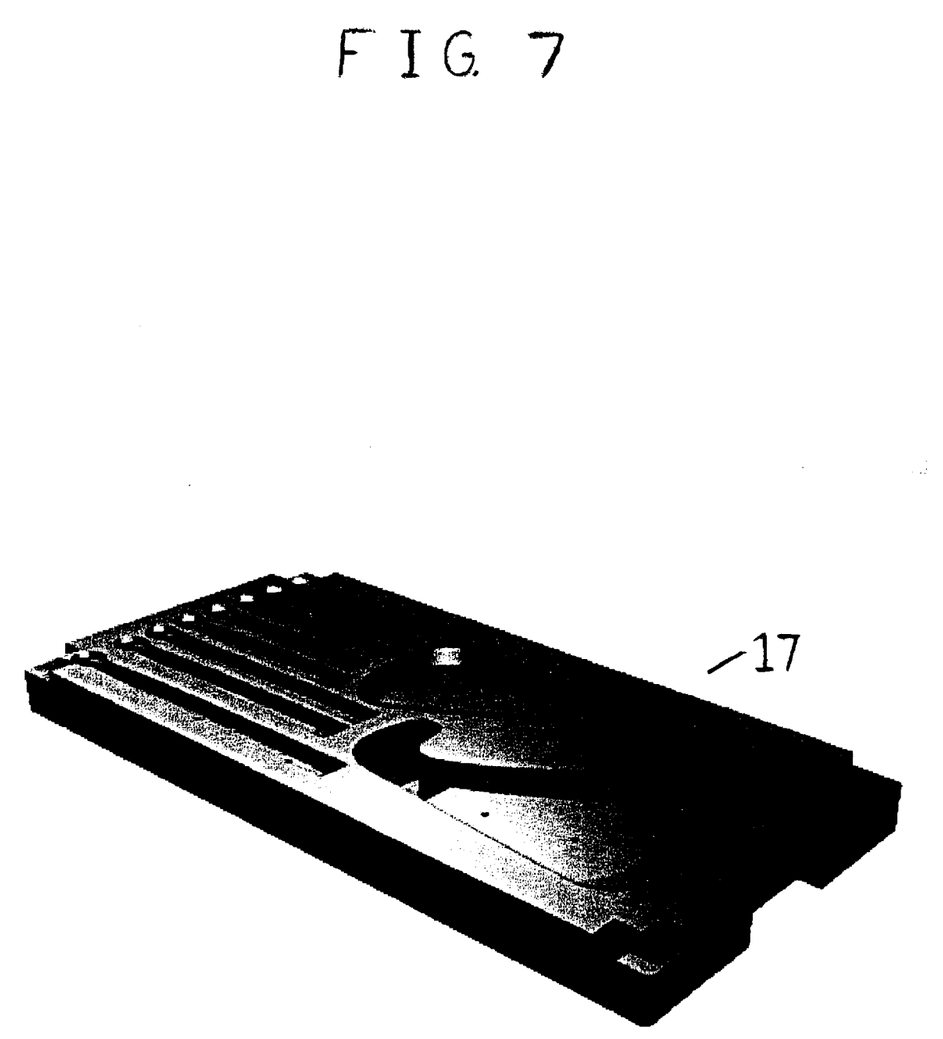
FIG. 7 is a perspective view of the bottom tier of the double tiered proffered embodiment of the apparatus, with no instruments positioned in the apparatus.
Figure 8:
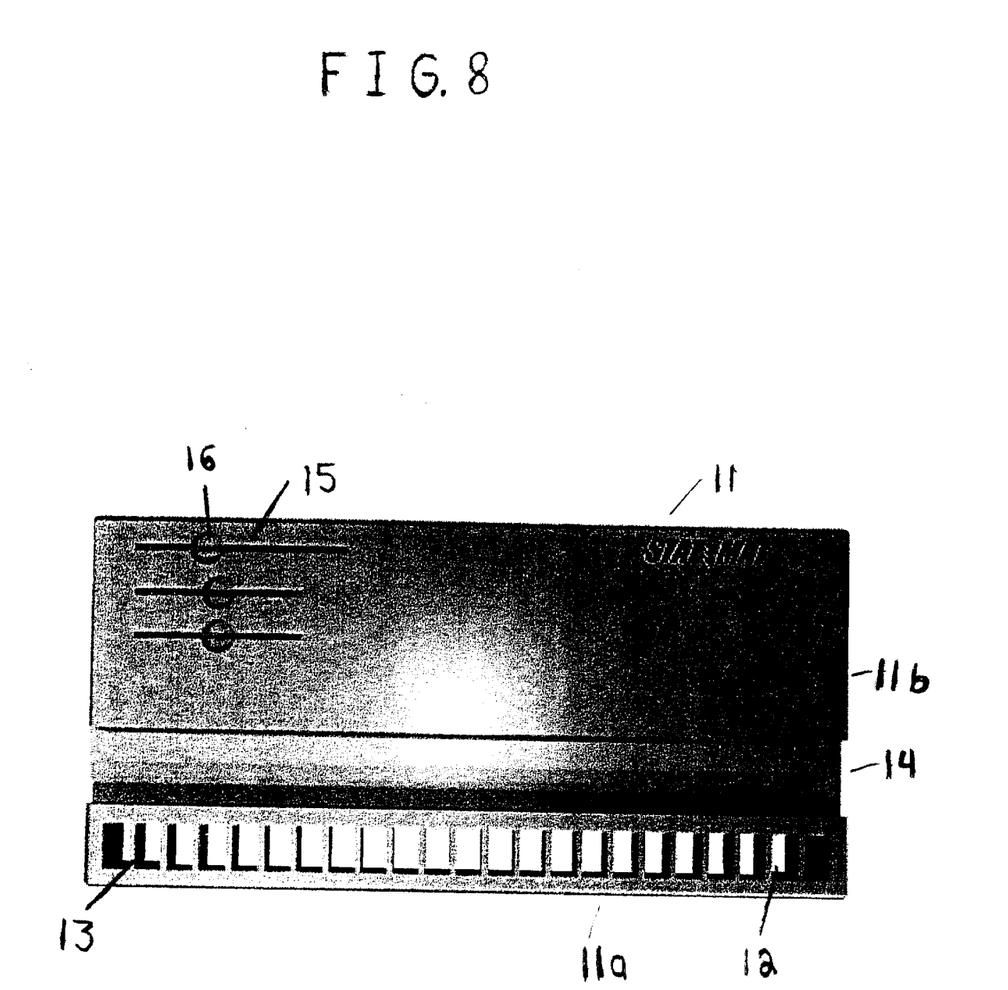
FIG. 8 is a top plan view of the top tier of the double tiered proffered embodiment of the apparatus, with no instruments positioned in the apparatus.
Figure 9:
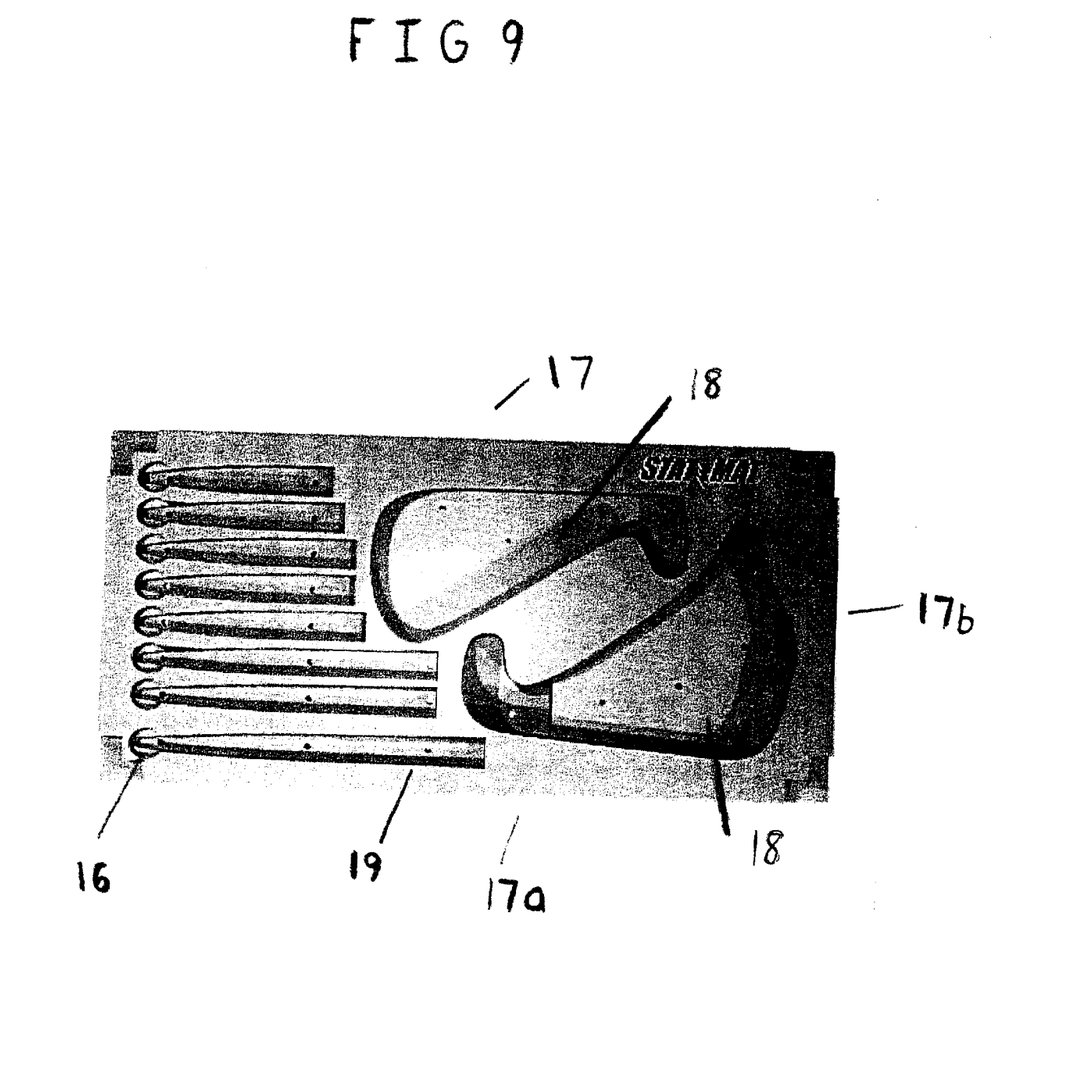
FIG. 9 is a top plan view of the bottom tier of the double tiered proffered embodiment of the apparatus, with no instruments positioned in the apparatus.

In a second preferred embodiment, exemplified in FIG. 5–FIG. 9, a two tiered apparatus 10 comprising an upper tray and a lower tray is envisioned. As shown in FIG. 5–FIG. 7, the upper tier is releasbly retained on top of the lower tier by way of legs attached to the upper tray which fit in grooves cut out of the lower tray. FIG. 5 illustrates the two tiered embodiment with both tiers stacked as they would be upon delivery to an operating room. As FIG. 8 and FIG. 9 illustrate, both upper and lower tier comprise two opposed, longitudinally oriented sides 11a and 17a respectively and two opposed widthwise oriented sides 11b and 17b, respectively, the longitudinally oriented sides 11a and 17a being substantially longer than the widthwise oriented sides 11b and 17b. As FIG. 6 demonstrates, the upper tier is comprised of two parallel longitudinally oriented sides and two parallel widthwise oriented sides, the longitudinally oriented sides being substantially longer than the widthwise oriented sides. The upper tier 11, as illustrated in FIG. 8 also comprises one longitudinally oriented, mortised, first rectangular channel 12, aligned substantially parallel and in close proximity to one of said longitudinally oriented sides of said tray 11a. The first channel 12, which may extend approximately 3 cm, deep does not span the entire length of the tray however and is defined as having two distinct end sections. A plurality of section dividers 13, which may be fixed or removably attached, are disposed in a perpendicular manner within said rectangular channel 12 and these section dividers may be separated by intervals of approximately 2 cm, or longer depending on the number of instruments to be retained. These section dividers may be spaced to securely retain at least two instruments in a ready position for operation room procedures.

A second rectangular channel 14, which runs the entire longitudinal distance of the tray, is positioned a distance from said first rectangular channel 12 and a further distance from said longitudinally oriented side. This second channel 14 is designed to allow the operating room assistant the ability to get a proper grip on the ring handled instruments in order to relay the instruments to the person performing the operation in accordance with proper operating room procedures. Up to and including ninety three (93) ringed instruments may be contained on the upper tier. Finally, the upper tier 11 may comprise a series of rectangular slots 15, disposed parallel to the second rectangular channel 14 and on the opposite side from the first rectangular channel 12. These rectangular slots 15 may be disposed with bevels 16 to facilitate removal of instruments contained within the slots. In a preferred embodiment, these slots may releasably retain mainly knife handles. In another preferred embodiment, three of these slots are present.

In FIG. 9, a preferred embodiment of the lower tier 17 illustrates two large mortised triangular grooves including arcuate edges 18, disposed at a close distance and parallel to either of said longitudinally oriented sides 17a and also disposed with opposing hypotenuses. Said triangular grooves 18 may be utilized to releasably retain instruments that comprise a straight handle and an arcuate operational surface. In one preferred embodiment, the instruments contained in said triangular groove 7 may be retractors. Up to and including four retractors may be contained in any one triangular groove.

Aligned parallel to said longitudinally oriented sides 17a are a series of mortised trapezoidal grooves 19, designed to releasably retain cylindrically shaped or flat, dual handled instruments. The length of these grooves is regulated by the size and position of said triangular grooves 18, as these trapezoidal grooves 19 span in a direction perpendicular to said triangular grooves 18. The trapezoidal shape of these slots acts as a bevel to allow a user to easily remove an instrument from the groove. A further bevel 16 may be added to the configuration at the end of the trapezoidal grooves, closest to the adjacent widthwise side 17b. The bevel 16 will allow the user easier instrument removal and also ensures that the technician handles the instrument properly so as to relay the instruments to the person performing the operation in accordance with proper operating room procedures.

In one preferred embodiment, these grooves may be adapted to contain forceps or other such instruments. As shown in FIG. 9, up to eight (8) of these slots may disposed, these slots varying in size to accommodate different sizes of instruments.

A major innovation created with the above described embodiments is the method of utilizing the system and the benefits the system creates. The method of preparing and utilizing instruments for an operating room procedure by stacking, sterilizing, transporting, delivering and maintaining the operating room instruments in proper operating room positions, along with saving operating room prep time, allows the instruments to be reused in a further operating room procedure, once the first operating room procedure has been completed.

The above preferred embodiments considered, it will be observed that numerous different configurations and alternatives may be achieved with out straying from the scope of the original invention. With this in mind, it is stated that no limitation with respect to the specific apparatus illustrated herein is intended or should be inferred. It is, of course, intended to cover by the appended claims all such modifications as are covered by the scope of the claims.

I claim:

1. A sterilizable apparatus for retaining surgical instruments comprising:

a surgical tray comprised of two opposed, longitudinally oriented sides and two opposed, widthwise oriented sides, said longitudinally oriented sides being substantially longer than the widthwise oriented sides;

a mortised, first rectangular channel, longitudinally oriented and aligned substantially parallel and at a close distance to a first of said longitudinally oriented sides of said tray;

a plurality of section dividers, removably attached and disposed in a manner perpendicular to the longitudinal span of said first channel set apart at intervals; wherein said section dividers are adapted to releasably and securely retain at least two ring handled instruments in a space defined by consecutively placed dividers;

a second rectangular channel, extending over the entire longitudinal distance of the tray, said second rectangular channel disposed at a distance from said first rectangular channel and at a further distance from said first longitudinally oriented side; wherein said second channel is disposed in such a manner to allow removal of instruments retained in said first rectangular channel;

a large mortised triangular shaped groove comprising arcuate edges and disposed at a distance from said second rectangular channel and on the opposing side from said first rectangular channel;

a plurality of mortised trapezoidal grooves, aligned parallel to said second rectangular groove, said trapezoidal grooves length regulated by the size and positioning of said triangular groove;

a plurality of mortised, small, thin rectangular slots;

wherein said first rectangular channel is disposed to retain at least one ring handled instrument in the proper position for operating room procedures.

2. The sterilizable apparatus for retaining surgical instruments of claim 1 wherein said first rectangular channel is disposed to retain a plurality of ring handled surgical instruments, a variable distance apart, and in the proper position for operating room procedures.

3. The sterilizable apparatus for retaining surgical instruments of claim 2 wherein said first rectangular channel is disposed to retain a plurality of ring handled surgical instruments in constant contact.

4. The sterilizable apparatus for retaining surgical instruments of claim 1 wherein said plurality of section dividers are set at a distance of 2 centimeters apart.

5. The sterilizable apparatus for retaining surgical instruments of claim 1 wherein the coaction between said first rectangular channel and said second rectangular channel allows an operating room assistant to maintain a proper grip on said ring handled instruments in order to relay said instruments a person performing an operation in accordance with proper operating room procedures.

6. The sterilizable apparatus for retaining surgical instruments of claim 1 wherein said triangular groove is utilized to retain instruments that comprise a straight handle and an arcuate operational surface.

7. The sterilizable apparatus for retaining surgical instruments of claim 6 wherein said triangular groove is disposed to retain retractors.

8. The sterilizable apparatus for retaining surgical instruments of claim 7 wherein said triangular groove is disposed to retain eight retractors.

9. The sterilizable apparatus for retaining surgical instruments of claim 1 wherein said trapazoidal grooves are disposed to releasably retain cylindrically shaped or flat, dual handled instruments.

10. The sterilizable apparatus for retaining surgical instruments of claim 9 wherein said trapezoidal grooves releasably retain forceps or other such instruments.

11. The sterilizable apparatus for retaining surgical instruments of claim 1 wherein said plurality of mortised, small, thin rectangular slots releasably retain knife handles.

12. The sterilizable apparatus for retaining surgical instruments of claim 1 wherein said plurality of section dividers are fixed and disposed in a manner perpendicular to the longitudinal span of said first rectangular channel.

13. The sterilizable apparatus for retaining surgical instruments of claim 1, wherein said instruments are in said ready position for operating room use throughout sterilization, transportation and delivery to an operating room.

14. The sterilizable apparatus for retaining surgical instruments of claim 1, wherein said apparatus is reusable for a next operation since said unused instruments are ready countable in an operation ready position.

15. A sterilizable apparatus for retaining surgical instruments comprising:

a pair of substantially rectangular instrument retaining trays comprising an upper tier and a lower tier; said upper tier comprising a plurality of upwardly concave grooves and said lower tier comprising a plurality of upwardly concave grooves, said grooves disposed to retain a plurality of surgical instruments; wherein said upper tier is releasably retained on top of said lower tier, wherein each of said plurality of upwardly concave grooves is employed to retain at least two surgical instruments, in a ready position for operation room procedures, wherein said upper tier further comprises:

a pair of opposed, longitudinally oriented sides and a pair of opposed widthwise oriented sides, said longitudinally oriented sides being substantially longer than said widthwise oriented sides;

a longitudinally oriented, mortised first rectangular channel, aligned substantially parallel and in close proximity to one of said longitudinally oriented sides of said upper tier; said channel disposed to retain ring handled instruments;

a plurality of section dividers removably attached in a substantially perpendicular manner within said rectangular channel, said section dividers placed at intervals defined by the amount of said instruments to be retained;

a second rectangular channel extending an entire length of said longitudinal sides and positioned a distance from said first rectangular channel and a further distance from said longitudinaily oriented side; said second channel disposed for proper removal of said ring handled instruments;

a plurality of rectangular slots disposed parallel to said second rectangular channel and disposed on the opposing side from said first rectangular channel; said slots disposed to retain knife handles, said slots disposed with bevels.

16. The sterilizable apparatus for retaining surgical instruments of claim 15 wherein said plurality of section dividers are fixed and disposed in a manner perpendicular to the longitudinal span of said first rectangular channel.

17. The sterilizable apparatus for retaining surgical instruments of claim 15 wherein said lower tier further comprises:

a pair of large, mortised triangular grooves including arcuate edges and aligned with opposing hypotenuses, said triangular grooves disposed at a close distance from and parallel to either of said longitudinally oriented sides; said triangular grooves utilized to releasably retain instruments comprising a straight handle and an arcuate operational surface.

a plurality of mortised trapezoidal grooves, aligned parallel to said longitudinally oriented sides of said lower tier, said trapezoidal grooves disposed to releasably retain cylindrically shaped or flat, dual handled instruments, said trapezoidal grooves further disposed with bevels.

18. The sterilizable apparatus for retaining surgical instruments of claim 17 wherein said triangular groove is disposed to retain retractors or other such instruments.

19. The sterilizable apparatus for retaining surgical instruments of claim 17 wherein said trapezoidal grooves releasably retain forceps or other such instruments.

* * * * *

UNITED STATES PATENT AND TRADEMARK OFFICE
CERTIFICATE OF CORRECTION

PATENT NO.     : 6,426,041 B2
DATED          : July 30, 2002
INVENTOR(S)    : Smith It is certified that error appears in the above-identified patent and that said Letters Patent is hereby corrected as shown below:

<u>Title page,</u>
Item [57], ABSTRACT,
Line 2, replace "nearly" with -- approximately --

<u>Column 2,</u>
Lines 38 and 39, delete "plastic or rubberized"

<u>Column 3,</u>
Line 7, replace "proffered" with -- preferred --
Line 10, replace "proffered" with -- preferred --
Line 14, replace "proffered" with -- preferred --
Line 19, replace "proffered" with -- preferred --
Line 22, replace "proffered" with -- preferred --
Line 26, replace "proffered" with -- preferred --
Line 29, replace "proffered" with -- preferred --
Line 33, replace "proffered" with -- preferred --
Line 36, replace "proffered" with -- preferred --

<u>Column 3,</u>
Line 39, replace "PREFERRED EMBODIMENT" with -- INVENTION --

<u>Column 5,</u>
Line 52, after "Up to and including," insert the following -- approximately --

Signed and Sealed this

Twenty-first Day of January, 2003

JAMES E. ROGAN
*Director of the United States Patent and Trademark Office*